US006495138B1

(12) United States Patent
van Nieuwstadt et al.

(10) Patent No.: US 6,495,138 B1
(45) Date of Patent: Dec. 17, 2002

(54) PRRSV ANTIGENIC SITES IDENTIFYING PEPTIDE SEQUENCES OF PRRS VIRUS FOR USE IN VACCINES OR DIAGNOSTIC ASSAYS

(75) Inventors: Antonie Paul van Nieuwstadt, Lelystad (NL); Jan Langeveld, Harderwijk (NL); Janneke Meulenberg, Amsterdam (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 09/434,476

(22) Filed: Nov. 5, 1999

Related U.S. Application Data

(63) Continuation of application No. PCT/NL98/00251, filed on May 5, 1998.

(30) Foreign Application Priority Data

May 6, 1997 (EP) .............................. 97201343

(51) Int. Cl.[7] .............................. A61K 39/12

(52) U.S. Cl. .............................. 424/186.1; 424/204.1; 424/211.1; 536/23.72; 530/327; 530/326; 530/328

(58) Field of Search .......................... 424/186.1, 204.1, 424/211.1; 536/23.72; 530/327, 326, 328

(56) References Cited

U.S. PATENT DOCUMENTS

| | | | |
|---|---|---|---|
| 5,476,778 | A | 12/1995 | Chladek et al. |
| 5,510,258 | A | 4/1996 | Sanderson et al. |
| 5,620,691 | A | 4/1997 | Wensvoort et al. |
| 5,677,429 | A | 10/1997 | Benfield |
| 5,683,865 | A | 11/1997 | Collins et al. |
| 5,690,940 | A | 11/1997 | Joo |
| 5,695,766 | A | 12/1997 | Paul et al. |
| 5,840,563 | A | 11/1998 | Chladek et al. |
| 5,846,805 | A | 12/1998 | Collins et al. |
| 6,197,310 | B1 | 3/2001 | Wensvoort et al. |
| 6,251,397 | B1 * | 6/2001 | Paul et al. ............. 424/186.1 |

FOREIGN PATENT DOCUMENTS

| | | |
|---|---|---|
| EP | 0 529 584 | 8/1992 |
| EP | 0 587 780 B1 | 3/1994 |
| EP | 0 610 250 B1 | 12/1995 |
| GB | 2 282 811 A | 4/1995 |
| GB | 2289279 | * 11/1995 |
| WO | WO 92/21375 | 12/1992 |
| WO | WO 93/03760 | 3/1993 |
| WO | WO 96/04010 | 2/1996 |
| WO | WO96/06619 | * 3/1996 |

OTHER PUBLICATIONS

Nieuwstadt et al .Journal of Virology, Jul. 1996, vol. 70, No. 7, pp. 4767–4772.*

Meulenberg et al . Virology, 1998, vol. 252, pp. 106–114.*
"Advances in Veterinary Virology 2", *Veterinary Microbiology*, 33 (1992), pp. 185–193.
Beale AJ, "Vaccines and antiviral drugs", *Principles of bacteriology, virology and immunity*, vol. 4, Ch. 86, pp. 147–161.
Boursnell et al., "Completion of the Sequence of the Genome of the Coronavirus Avian Infectious Bronchitis Virus", *Journal of General Virology* 68, 1986, pp. 57–77.
Brinton MA, "Lactate Dehydrogenase–Elevating, Equine Arteritis and Lelystad Viruses", *Encyclopedia of Virology*, vol. 2, pp. 763–771.
Christianson et al., "Experimental reproduction of swine infertility and respiratory syndrome in pregnant sows", *Am J Vet Res.*, vol. 53, No. 4, Apr. 1992, pp. 485–488.
Christianson et al., "Porcine reproductive and respiratory syndrome: A review", *Swine Health and Production*, vol. 2, No. 2, pp. 10–28, Mar. and Apr., 1994.
Collins et al., "Isolation of swine infertility and respiratory syndrome virus (isolate ATCC VR–2332) in North America and experimental reproduction of the disease in gnotobiotic pigs", *J Vet Diagn Invest*, 4:117–126 (1992).
Dea et al., "Swine reproductive and respiratory syndrome in Quebec: Isolation of an enveloped virus serologically–related to Lelystad virus", *Can. Vet. Journal*, vol. 33, pp. 801–808.
Den Boon et al., "Equine Arteritis Virus Is Not a Togavirus but Belongs to the Coronaviruslike Superfamily", *Journal of Virology*, vol. 65, No. 6, pp. 2910–2920, 1991.
de Vries et al., "All subgenomic mRNAs of equine arteritis virus contain a common leader sequence", *Nucleic Acids Research*, vol. 18, No. 11, 1990, pp. 3241–3247.
"Diseases Of Swine", Sixth Edition, Iowa State University Press, 1986, pp. 244–315.
Duran et al., "Recombinant Baculovirus Vaccines Against Porcine Reproductive And Respiratory Syndrome (PRRS)", *Abstracts PRRS*, Aug. 9th to 10th, 1995, Copenhagen, Denmark, 2 pages.
Dykhuizen et al., "Determining the Economic Impact of the 'New' Pig Disease", *Porcine Reproductive and Respiratory Syndrome*, A Report on the Seminar Held in Brussels on Nov. 4–5, 1991 and Organized by the European Commission, pp. 53–60.
Fenner et al., "Viral Genetics and Evolution", *Veterinary Virology*, Ch. 5, pp. 89–95.
Fenner et al., "Immunization against Viral Diseases", *Veterinary Virology*, Ch. 14, pp. 265–271.

(List continued on next page.)

Primary Examiner—Ali R. Salimi
(74) Attorney, Agent, or Firm—TraskBritt

(57) ABSTRACT

The invention provides antigenic sites of PRRSV isolates. The antigenic sites are neutralizing, conserved, non-conserved and conformational, can elicit antibodies and are found on protein GP4 and N encoded ORF4 and ORF7 of PRRSV. The peptide sequences identified by the sites can be incorporated in vaccines directed against PRRS and in diagnostic tests for PRRS. Also, discriminating tests can be developed that can be used next to marker vaccines in programs designed to eradicate PRRS from pig herds.

3 Claims, 9 Drawing Sheets

OTHER PUBLICATIONS

Godeny et al., "Map Location of Lactate Dehydrogenase–Elevating Virus (LDV) Capsid Protein (Vp1) Gene", *Virology* 177, (1990), pp. 768–771 (1990).

Godeny et al., "The 3' Terminus of Lactate Dehydrogenase–Elevating Virus Genome RNA Does Not Contain Togavirus or Flavivirus Conserved Sequences", *Virology 172*, pp. 647–650 (1989).

Goyal et al., "Porcine reproductive and respiratory syndrome", *J. Vet. Diagn. Invest.*, vol. 3, pp. 656–664.

Joo et al., "Encephalomyocarditis Virus As A Potential Cause For Mystery Swine Disease", *Livestock Conservation Institute*, Denver, CO, pp. 62–66, Oct. 6, 1990.

Keffaber, K., "Reproductive Failure of Unknown Etiology", *AASP Newsletter*, vol. 1, No. 2, Sep.–Oct. 1989, pp. 1, 4–5, 8–10.

Kuo et al., "A Nested Set of Eight RNAs Is Formed in Macrophages Infected with Lactate Dehydrogenase–Elevating Virus", *Journal of Virology*, vol. 65, No. 9, Sep. 1991, pp. 5118–5123.

Loula, Timothy, "Mystery Pig Disease", *Agri–Practice*, vol. 12, No. 1, pp. 29–34, Jan./Feb. 1991, 7 pages.

Mc Cullough et al., "9. Experimental Transmission Of Mystery Swine Disease", *The New Pig Disease Porcine Respiration And Reproductive Syndrome*, A report on the seminar/workshop held in Brussels on Apr. 29–30, 1991, pp. 46–52.

Meredith MJ, "Porcine Reproductive and Respiratory Syndrome (PRRS)", Pig Disease Information Center, 1st North American Edition, University of Cambridge, pp. 1–57, Aug. 1994.

Moormann et al., "Molecular Cloning and Nucleotide Sequence of Hog Cholera Virus Strain Brescia and Mapping of the Genomic Region Encoding Envelope Protein $E1^{1}$", *Virology 177*, pp. 184–198 (1990).

Morrison et al., "Brief Communications Serologic evidence incriminating a recently isolated virus (ATCC VR–2332) as the cause of swine infertility and respiratory syndrome (SIRS)", *J Vet Diagn Invest*, 4:186–188 (1992).

Murphy et al., "Immunization Against Virus" in *Virology* 2nd ed., vol. 1, Fields et al. eds. Raven Press, NY, 1990, pp. 469–502.

Notice of Opposition by Akzo Nobel against European Patent No. 0 587 780, Nov. 28, 1995, EP.

Notice of Opposition by Cyandmid Iberica against European Patent No. 0 587 780 Nov. 28, 1995, EP.

Pathological, ultrastructural, and immunohistochemical changes caused by . . . , *The Veterinary Quarterly*, vol. 13, No. 3, Jul. 1991, pp. 137–143.

Pol et al., "Pathological, ultrastructural, and immunohistochemical changes caused by Lelystad virus in experimentally induced infections of mystery swine disease (synonym: porcine epidemic abortion and respiratory syndrome (PEARS))", *The Veterinary Quarterly*, vol. 13, No. 3, Jul. 1991, pp. 137–143.

Polson DD, "Answers to Your Questions on PRRS", NOBL Laboratories, 18 pages.

Polson DD, "RespPRRS A PRRS Vaccine Review", NOBL Laboratories, 22 pages.

Polson et al., "An evaluation of the financial impact of Porcine Reproductive and Respiratory Syndrome (PRRS) in nursery pigs", *Proceedings of the 13th International Pig Veterinary Society Congress*, p. 31, Jun. 1994.

Polson et al., "Financial Implications of Mystery Swine Disease (MSD)", pp. 8–28.

Response to Opposition to European Patent No. 0 587 780, Aug. 30, 1996.

"Revision of the taxonomy of the Coronavirus, Torovirus and Arterivirus genera", *Arch Virol*, vol. 135, pp. 227–239, 1994.

Saif L.S., "Coronavirus immunogens", *Veterinary Microbiology*, 37:285–297, 1993.

Scott F.W., "Immunization Against Feline Coronaviruses", *Adv. Exp. Med. Biol.*, 218:569–576, 1987.

Snijder et al., "The carboxyl–terminal part of the putative Berne virus polymerase is expressed by ribosomal frameshifting and contains sequence motifs which indicate that toro– and coronaviruses are evolutionarily related", *Nucleic Acids Research*, vol. 18, No. 15, pp. 4535–4542, 1990.

Terpstra et al., "Experimental reproduction of porcine epidemic abortion and respiratory syndrome (mystery induced infections of mystery swine disease (synonym: porcine epidemic abortion and respiratory symdrome (PEARS)", *The Veterinary Quarterly*, vol. 13, No. 3, Jul. 1991, pp. 131–136.

Timony PJ, "Equine Viral Arteritis", *Manual of Standards for Diagnostic Tests and Vaccines*, pp. 493–499, 1992.

van Zijl et al., "Live Attenuated Pseudorabies Virus Expressing Envelope Glycoprotein E1 of Hog Cholera Virus Protects Swine against both Pseudorabies and Hog Cholera", *Journal of Virology*, vol. 65, No. 5, May 1991, pp. 2761–2765.

*Veterinary Bulletin*, vol. 58, No. 11, 1988, No.'s 6903–6909, p. 932.

*Veterinary Bulletin*, vol. 60, No. 3, 1990, No.'s 1536–1551, pp. 255–256.

Visser, Nicolaas, "Declaration Of Dr. N. Visser", Nov. 14, 1995, pp. 1–11.

von V. F. Ohlinger et al., "Der 'Seuchenhafte Spatabort beim Schwein'—Ein Beitrag zur Atiologie des"Porcine Reproductive and Respiratory Syndrome (PRRS)"", *Tierarztl*.

Waltner–Towes et al., "A Field Trial to Evaluate the Efficacy of a Combined Rotavirus–Coronavirus/*Escherichia coli* Vaccine in Dairy Cattle", *Can. J. Comp. Med.*, 49:1–9, 1985.

Wardley et al., "The Host Response to African Swine Fever Virus", *Prog. med. Virol.*, vol. 34, pp. 180–192, (1987).

Wenswoort et al., "Antigenic comparison of Lelystad virus and swine infertility and respiratory syndrome (SIRS) virus", *J Vet Diagn Invest*, vol. 4, pp. 134–138, 1992.

Wensvoort et al., "Blue ear" disease, *The Veterinary Record*, vol. 128, No. 128, Jun. 15, 1991, column 1, letter, p. 574.

Wensvoort et al., "Mystery swine disease in the Netherlands: the isolation of Lelystad virus", *The Veterinary Quarterly*, vol. 13, No. 3, Jul. 1991, pp. 121–130.

Wensvoort et al., "The Porcine Reproductive and Respiratory Syndrome; Characteristics and diagnosis of the causative virus", *Veterinary Biotechnology Newsletter*, vol. 3, pp. 113–120, 1993.

Yoon et al., "Isolation of a cytophathic virus from weak pigs on farms with a history of swine infertility and respiratory syndrome", *J. Vet. Diagn Invest*, 4:139–143 (1992).

Abstracts of Papers Presented at the 71st Annual Meeting of the Conference of Research Workers in Animal Disease, No.'s 1–6, Nov. 5–6, 1990, 2 pages.

"Dutch Team Isolates Mystery Pig Disease Agent," *Animal Pharm*, 230, p. 21, Jun. 21, 1991.

PCT International Preliminary Examination Report, PCT/NL98/00251, dated Aug. 2, 1999.

* cited by examiner

Fig. 3A Alignment of amino acids of GP₄ of PRRSV isolates

```
I-1102-4     MAAATLFFLAGAQHIMVSEAFACKPCFSTHLSDIETNTTAAAGFMVLQDI           50
NL1-4                                                                    50
NY2-4                   L                                                50
PRRSV10-4               L                                                50
LUX-4                   L                           K                    50
SPA1-4            I     S  F                        K              N     50
FRA-4             I  L     F                        K              N     50
DEN-4             I  L     L                        K                    50
VR2332-4         SSL LVV FKCLL  Q              SS A K         S A        50
IA1-4             SL L V FKCLL  Q              SS A K         S A   E    50
KS1-4             SL LMV FKCLL  Q              SS A K         SSV        50
MN1-4             SL LMV FKCLL  Q              SS A K         S A        50
IA6-4             SL L V FKCLL  Q              SS A K         S A        50
IL1-4             SL L V FKCFV  Q              SS A K         N A   E    50
NE1-4            SSL LMV FKCLL  Q              SS A K         G A   E    50
SG1-4             SL L V FKCLL  Q      NQ      SS E K         G A        50
VR2385-4          SL L V FKCLL  Q              SS   K                    50
KY1-4             SL LMV FKCLL  Q              SS A K         S A        50
MO1-4             SL LMV FERLL  Q              SS A K         G A   E    50
                 **.. **.... . ..**.****..***. *...*.*******. ***.*

I-1102-4     NCFRPHGVSAAQEKISFGKSSQCREAVGTPQYITITANVTDESYLYNADL          100
NL1-4                                                                   100
NY2-4                                                                   100
PRRSV10-4                                                               100
LUX-4                L     R       E                                    100
SPA1-4               L     T     N P    P          I                    100
FRA-4                L     T     N      P          I                    100
DEN-4         T A    A   EESQSVT N      P          I          H         100
VR2332-4      S L   HRDSASE----AIR IP        T I   V V        N HSS      96
IA-4          S L   HRNSASE----AIR VP        T I   V          N HSS      96
KS1-4         S L   HRNSASE----AIR VP  Y     T I   V          N HSS      96
MN1-4         S L   HRNSASE----AIR IP        A I   V          N HSS      96
IA6-4         S L   HRDSASE----AIR  P        T I   V          N HSS      96
IL1-4         S L   HRDSASE----AIR IP        T I   V          N HSS      96
NE1-4         S L   HRNPAPE----A R IP        T I   V  SV      N HSS      96
SG1-4         S L   HRNPAPE----AIR VP        T I   V          N HSS.     96
VR2385-4      S L   HRNSASE----AIR VP        T I   V  V       N HSS      96
KY1-4         S L   HRDSAFE----T R VP        T I   V  V       N HSS      96
MO1-4         S L   HRDSTSE----AFR VP        T I   V  V       N HSS      96
              .* *.. . .   .. * .*.*.*.*.* *...******.**...**
```

Fig. 3A continued

```
I-1102-4      LMLSACLFYASEMSEKGFKVIFGNVSGVVSACVNFTDYVAHVTQHTQQHH    150
NL1-4                                                              150
NY2-4                                                              150
PRRSV10-4                                                          150
LUX-4                                                              150
SPA1-4                                                             150
FRA-4                                                              150
DEN-4                                                              150
VR2332-4        S              V         I AV      S Q  KEF  -RS   145
IA1-4           S            E V         I AV      S Q  REF  -RS   145
KS1-4           S            E V         I AV      S Q  REF  -RS   145
MN1-4           S            E V         I AV      S Q  REF  -RS   145
IA6-4           S              V          IAAV     S Q  KES  -RS   145
IL1-4           S            E V         I AV      S Q  REF  -RS   145
NE1-4           S              V         I AV      S Q  KEF  -RS   145
SG1-4           S              V         I AV      S Q  KEF  -RS   145
VR2385-4        S              V         I AV      S Q  KEF  -RS   145
KY1-4           S              V           AV      S Q IKEF  -PS   145
MO1-4           S              V           AV      S Q IKEF  -RS   145
              **** .************* . ****** .... **** . ** . * . . ** .

I-1102-4      LVIDHIRLLHFLTPSAMRWATTIACLFAILLAI    183
NL1-4                                             183
NY2-4                                             183
PRRSV10-4                                         183
LUX-4                                             183
SPA1-4                        T                   183
FRA-4                         T                   183
DEN-4         A                                   183
VR2332-4      V  V      M  ET    VL               178
IA1-4         MV V      M  ET    VL               178
KS1-4         MV V      M  ET    VL               178
MN1-4         MV V      M  ET    FL     G         178
IA6-4         V  V      M  ET    VL               178
IL1-4         V  V      M  ET    VL               178
NE1-4         V  V      M  ET    VL F             178
SG1-4         V  V      M  ET    VL               178
VR2385-4      V  V      M  ET    VL       T       178
KY1-4         V  V F    I  ET    VL     G  ---    175
MO1-4         V  V      I  ET    FL     G  ---    175
              * .**.*.***.**..*****.*  *  .**
```

Fig. 3B Alignment of amino acid sequences of N of PRRSV isolates

```
I-1102-7    MAGKNQSQKKKKSTAPMGNGQPVNQLCQLLGAMIKSQ---RQQPRGGQAK        47
PRRSV10-7                                                                47
VR2332-7        PNN GK TEE ----K D      M KI AQ NQS GKGP KKN      46
NE1-7           PNN GK TEE ----R D      M KI AQ NQS GKGP KKN      46
IL1-7           PNN GK P E ----K D      M KI AQ NQS GKGP KKN      46
IA1-7           PNN GK Q   ----K D      M KI AQ NQS GKGP KKNR     46
IA6-7           PNN GK QN  ----K D      M KI AQ NQS GKGP KKN      46
KS1-7           PHN GK Q R ----K D      M KI AQ NQS GKGP KKF      46
MN1-7           PNN GK Q R ----K D      M KI AQ NQS GKGP KKN      46
SG1-7           PNN GR Q   ----K DC     M KI AQ NQS GKGP KKI      46
MO1-7           PNN GR Q   ----K D      M KI AQ NQS GKGP QIN      46
KY1-7           PHN GR Q   ----K D      M KI AQ NQS GKGP KKN      46
ISU3927-7       PNN GK Q   ----K D      M KI AQ NQS GKGP KKN      46
ISU55-7         PNN GK Q   ----K D      M KI AQ NQS GKGP KKN      46
ISU1894-7       PNN GK Q R ----K D      M KI AQ NQS GKGP KKN      46
VR2385-7        PNNTGK Q R ----K D      M KI AH NQS GKGP KKN      46
IAF-7           PNN GR Q   ----K D      M KI AQ NQS GKGP KKN      46
                 *. .. .*. *       .*. ********.** .* *   *  ..*   .

I-1102-7    KKKPEKPHFPLAAEDDIRHHLTQTERSLCLQSIQTAFNQGAGTASLSSSG        97
PRRSV10-7                                       P                        97
VR2332-7        N       T   V     F PS  Q   S           CT  D     96
NE1-7           T       T   V     F PS  Q   S           CT  D     96
IL1-7           N       T   V :   F PS  Q   S           CT  D     96
IA1-7           N       T   V     F PS  Q   S           CI  D     96
IA6-7           N       T   V     F PS  Q   S           CT  D     96
KS1-7           N       T   V     F PS  Q   S           CT  D     96
MN1-7           N       T   V     F PS  Q   S           ICI D     96
SG1-7           N         T V V   F PS  Q   S           CT  D     96
MO1-7           N          SI FV  F PS  Q   S           CT  D     96
KY1-7          IN V    YS VT  V   F PS  Q   S           CI  D     96
ISU3927-7       N       T   V     F PS  Q   S           CT  D     96
ISU55-7         N       T   V     F SG  Q   S           CT  D     96
ISU1894-7       N       T   V     F PS  Q   S           CT  D     96
VR2385-7        N       T   V     F PS  Q   S           CT  D     96
IAF-7           N       T   V     F PS  Q   S           CT  D     96
                 * .* **. **    *  .***.*...** ***  ************.  **.**

I-1102-7    KVSFQVEFMLPVAHTVRLIRVTSTSASQGAS       128
PRRSV10-7                                         128
VR2332-7    RI YT  S    TH           ASPSA----   123
NE1-7       RI YT  S    TH ·         ASPSA----   123
IL1-7       RI YT  S    TH           APSSA----   123
IA1-7       RI YT  S    TH           ASPSA----   123
IA6-7       RI YT  S    TH           APPSA----   123
KS1-7       RI YT  S    TH           ASPSA----   123
MN1-7       RI YT  S    TH           VSPSA----   123
SG1-7       RI YT  S    TH           ASPSA----   123
MO1-7       RI YT  S    TH           ASPSA----   123
KY1-7       RI YT  S    TH           ASPSA----   123
ISU3927-7   RI YT  S    TH           APPSA----   123
ISU55-7     RI YT  S    TH           APPSA----   123
ISU1894-7   RI YT  S    TH           ASPSA----   123
VR2385-7    RI YT  S    TH           ASPSA----   123
IAF-7       RI YA  S    TH           ASPSA----   123
            ..*. *** **. ********  ....
```

Fig. 4

```
              A                    B                       C
VR2332   MPNNNGKQTEEK----KGDGQPVNQLCQMLGKIIAQQNQSRGKGPGKKN    45
         |   |||| ||     | || ||||| | ||||| |   |  |   |
LV       MAGKNQSQKKKKSTAPMGNGQPVNQLCQLLGAMIKSQ---RQQPRGGQA   46
           |||||||     |  | || | ||| ||| | |    |  | |
LDV      M-----SQNKKKSGQNKGANQ---QLNQLINALLRNAGQNKGKG----Q   37
                               D   RMF

D                              D
VR2332   KKKNPEKPHFPLATEDDVRHHFTPSERQLCLSSIQTAFNQGAGTCTLSDS    95
         ||| |||||||||| || ||| ||  |||| || |||||||||| || |
LV       KKKKPEKPHFPLAAEDDIRHHLTQTERSLCLQSIQTAFNQGAGTASLSSS    96
         ||||  | || ||  | | || ||||  |||| ||  ||  |||| || |
LDV      KKKKQPKLHFPMAGPSDLRHVMTPNEVQMCRSSLVTLFNQGGGQCTLVDS    87

VR2332   GRISYTVEFSLPTHHTVRLIRVTASPSA----   123
         |  |  ||| |  | |||||||| |  |
LV       GKVSFQVEFMLPVAHTVRLIRVTSTSASQGAS   128
         |   | ||| || | ||||| |||  |
LDV      GGINFTVSFMLPTHATVRLINASANSSA----   115
```

PRRSV ANTIGENIC SITES IDENTIFYING PEPTIDE SEQUENCES OF PRRS VIRUS FOR USE IN VACCINES OR DIAGNOSTIC ASSAYS

CROSS REFERENCE TO RELATED APPLICATION

This application is a continuation of pending International Application No. PCT/NL98/00251, filed on May 5, 1998 designating the United States of America.

TECHNICAL FIELD

The invention relates to the causative agent of Mystery Swine Disease, the PRRS virus, to peptide sequences identified in the PRRS virus, and to incorporating these sequences in vaccines and diagnostic tests.

BACKGROUND

PRRS virus (PRRSV) is the causative agent of a pig disease, currently called porcine reproductive and respiratory syndrome (PRRS). The virus is the causative agent of a pig disease, seen since approximately 1987 in the U.S. and since 1990 in Europe, known initially under various names such as Mystery Swine Disease, Swine Infertility and Respiratory Syndrome, and many more. The virus itself was also given many names, among which Lelystad virus (LV), SIRS virus, and many more, but is now mostly designated porcine reproductive and respiratory syndrome virus (PRRSV). It causes abortions and respiratory distress in pigs and was first isolated in Europe in 1991 (EP patent 587780, U.S. Pat. No. 5,620,691) and subsequently in the U.S. and many other countries throughout the world. PRRSV is a small enveloped virus containing a positive strand RNA genome. PRRSV preferentially grows in macrophages. In addition to macrophages, PRRSV can grow in cell line CL2621 and other cell lines cloned from the monkey kidney cell line MA-104 (Benfield et al., *J. Vet. Diagn. Invest.* 4; 127–133, 1992). The genome of PRRSV, a polyadenylated RNA of approximately 15 kb was sequenced in 1993 (Meulenberg et al., Virology 192; 62–74, 1993). The nucleotide sequence, genome organization and replication strategy indicated that PRRSV is related to a group of small enveloped positive-strand RNA viruses, designated Arteriviruses. This group includes lactate dehydrogenase-elevating virus (LDV), equine arteritis virus (EAV), and simian hemorrhagic fever virus (SHFV). These viruses have a similar genome organization, replication strategy, morphology, and amino acid sequence of viral proteins. Arteriviruses contain a genome of 12.5 to 15 kb and synthesize a 3' nested set of six subgenomic RNAs during replication. These subgenomic RNAs contain a leader sequence which is derived from the 5' end of the viral genome. ORFs 1a and 1b comprise approximately two thirds of the viral genome and encode the RNA dependent RNA polymerase. Six smaller ORFs, ORFs 2 to 7, are located at the 3' end of the viral genome. ORFs 2 to 6 likely encode envelope proteins whereas ORF7 encodes the nucleocapsid protein (Meulenberg et al, *Virology* 206; 155–163, 1995).

PRRSV is the first Arterivirus for which it has been demonstrated that all six proteins encoded by ORFs 2 to 7 are associated with the virion. The 15-kDa N protein (encoded by ORF7) and the 18-kDa integral membrane protein M (ORF6) are not N-glycosylated, whereas the 29- to 30-kDa $GP_2$ protein (ORF2), the 45- to 50-kDa protein $GP_3$ protein (ORF3), the 31-to 35-kDa $GP_4$ protein (ORF4), and the 25-kDa protein $GP_5$ (ORF5) are. These proteins have also been detected in extracellular virus and lysates of cells infected with a North American isolate of PRRSV, ATCC-VR2332, and other isolates of PRRSV (other isolates of PRRSV are for example CNCM I-1140, ECACC V93070108, CNCM I-1387, CNCM I-1388, ATCC-VR2402, ATCC-VR2429. ATCC-VR2430, ATCC-VR2431, ATCC-VR2475, ATCC-VR2385, but many others are known).

We earlier described the isolation and characterization of a panel of PRRSV-specific MAbs that were specific for $GP_3$, $GP_4$, M and N (van Nieuwstadt et al., J. Virol. 70,4767–4772, 1996). Interestingly, MAbs directed against $GP_4$ were neutralizing, suggesting that at least part of the protein is exposed at the virion surface. Furthermore, most of the Mabs directed against N reacted with all PRRSV isolates tested.

PRRS in it self is a problem of major concern for the swine industry in most parts of the world. Introduction of PRRSV in pig herds will cause severe economic losses. Diagnostic testing against PRRS is widely practiced by many veterinarians and laboratories. Most diagnostic tests, such as IPMA, IFT, IFA, ELISA, each comprising suitable means of detection such as conjugated enzymes or fluorochromes, and other substrates, use interactions between antigen derived from PRRSV and antibodies directed against PRRSV to measure the presence of either PRRSV antigen or antibodies directed against PRRSV in a biological sample, such as blood, serum, tissue, tissue fluids, lavage fluids, urine, feces, that is sampled from the animal (such as a pig) to be tested. The antigen and/or antibodies used in these diagnostic tests, or diagnostic kits or assays, for PRRS diagnosis are only defined by their origin from, or by their reactivity with PRRSV. In principle this suffices for screening assays where a high specificity or sensitivity is not explicitly required. However, the ever continuing spread of PRRS has caused great concern among the pig industry, to the extent that it is deemed needed to eradicate PRRS from whole herds, or even from complete areas, regions, or countries where pigs are raised. A clear example of this need is the proposed eradication program relating to PRRS in Denmark. If one decides to completely eradicate PRRS then diagnostic tests are needed that exhibit higher specificity or sensitivity than the tests used today.

Vaccination against PRRS is also widely practiced. Several examples are known of modified live vaccines that are used, and also killed vaccines are known. However, a problem with live vaccines in general, and thus also with live PRRS vaccines, exists in that these vaccines have a tendency to spread to non-vaccinated pigs, thereby spreading instead of reducing detectable infection in pig herds, and thus being counter productive to complete eradication. If a line marker vaccine were used that could serologically be differentiated from the wild type virus, then this problem would be greatly reduced. Added disadvantages are that live vaccines sometimes cause anaphylactic reactions in the vaccinated pigs, because of undefined antigenic components. Although killed vaccines in general are reported to induce protection in the vaccinated pig, and have the additional advantage that they do not spread from pig to pig, a disadvantage of killed vaccines is that it may be hard to accrue sufficient antigenic mass in one dose of a vaccine to elicit a measurable and protective immune response. Especially killed vaccines that can induce measurable neutralizing antibody titers in pigs would be beneficial to have since measuring these neutralizing antibodies in vaccinated pig populations would help generate understanding about the level of protection obtained by vaccination in the pig herd.

In addition, if one succeeds in assembling the necessary antigenic mass, this also means that more and other undefined antigenic mass is also present in the vaccine, which can also give rise to the anaphylactic reactions as described above. In this sense it would be beneficial to know which specific site on PRRSV is important peptide sequences needed for eliciting neutralizing antibodies. An advantage of the currently used vaccines originating from PRRSV isolates isolated in the U.S. is that such vaccines, albeit fully protective against and immunologically cross-reactive with European isolates of PRRSV, contain, as yet undefined, epitopes or antigenic sites by which they can be discerned from European isolates of PRRSV. Reciprocally, live vaccines originating from PRRSV isolates isolated in Europe, albeit fully protective against and immunologically cross-reactive with U.S. isolates of PRRSV, contain similar as yet undefined epitopes or antigenic sites by which they can be discerned from U.S. isolates of PRRSV.

If serological tests would be available which could discriminate (based on the small epitopic differences between PRRSV isolates) between pigs that are either vaccinated with a U.S. derived vaccine or infected with a European wild type of PRRSV (being vaccinated or not), or which could discriminate pigs that are either vaccinated with a European derived vaccine or infected with an U.S. wild type of PRRSV (being vaccinated or no), than marker vaccines and corresponding diagnostic tests (incorporating said discerning epitopes or antigenic sites) could be developed which could be used with large confidence in eradication programs for PRRS. For example, in Denmark it would than be possible to vaccinate with a U.S. derived vaccine and measure the set of antibodies in the Danish pigs which are solely directed against unique epitopes on European wild types of PRRSV and not cross-reactive with U.S. strains. This would enable the unequivocal detection and subsequent removal of wild type infected pigs from Danish herds. Currently, such a discrimination is not possible due to the overall broad immunological cross-reactivity between PRRSV isolates. It goes without saying that such combined vaccination-testing programs will be the basis for eradication of PRRS, and can also be used in other countries, if needed with distinct PRRSV antigenic sites being used in vaccine and/or diagnostic test.

DISCLOSURE OF THE INVENTION

The invention now provides antigenic sites comprising peptide sequences of PRRSV which allow the improvement of vaccines, be it killed or attenuated vaccines or vaccines derived via recombinant DNA technology, and antigenic sites which allow the improvement of diagnostic methods, tests and kits and the production of new diagnostic methods, tests and kits. Artificial changes or amino acid residue substitutions that maintain the antigenicity (as for example defined by the reactivity with polyclonal sera or MAbs) and thus functionality of the antigenic site can easily be derived from sequences known to constitute an antigenic site of a specific isolate by a person with ordinary skills in the art of peptide design and synthesis. For example, certain amino acid residues can conventionally be replaced by others of comparable nature, e.g. a basic residue by another basic residue, an acid by an acid, a bulky by a bulky, a hydrophobic or hydrophilic by another hydrophobic or hydrophilic residue, and so on. Also, other, less conventional but more specific changes are also possible that maintain or even improve the antigenicity of the selected sequence. Such changes can for example be made by PEPSCAN based amino acid substitutions or replacement mapping techniques (van Amerongen et. al., Peptide Research (1992) 5,269–274). In short, amino acid residues within the antigenic sites provided by the invention can e.g. be replaced conventionally or under guidance of replacement mapping, whereby the resulting peptide sequences are functionally equivalent to the antigenic site. The replacing amino acids can be either L- or D-amino acid residues. In addition, the peptide sequences provided by the invention are rendered even more immunogenic by conjugating them to adjuvants (such as KLH) known in the art. Additionally, the peptides are rendered even more immunogenic by making peptides with one (such as tandem peptides) or more repeated sequences or by polymerization or circularization.

Although it has been shown before that the N protein is immunogenic (Meulenberg (1995), J. Clin. Diagn. Lab. Immunol. 2, 652–656, GB 2 289 279 A) and that conserved and nonconserved regions between the N protein of European strains (LV) and U.S. strains (VR2332) exist (WO 96/04010), we demonstrate here for the first time which conserved and nonconserved regions are antigenic and which can be used individually or in combinations as antigens for immunization or diagnostic assays. Furthermore it is identified here that the antigenic regions in the N protein consist both of linear and conformation dependent epitopes.

The GP4 protein is the first structural protein of PRRSV for which is shown that it elicits antibodies that can neutralize the virus. A specific region of approximately 40 amino acids was identified and defined that should be exposed at the virion surface as a target for neutralizing antibodies, which then prevent the virus to infect the cells. This is an exciting new finding since it is generally assumed that the GP5 protein, the major structural of PRRSV, is the most important candidate involved in the attachment of the host cell.

The invention provides a major antigenic site, a neutralization site on $GP_4$ of PRRSV. The invention provides the localization of a major neutralization site important for the design of effective marker vaccines that comprise amino acid core sequences and amino acid sequences flanking the core sequences of PRRSV isolates which sequences comprise the neutralization site on the ORF4 protein of PRRSV. By incorporating the relevant neutralization site sequences in the various types of vaccines, it is possible to specifically induce neutralizing antibodies in the vaccinated pig. Killed vaccines comprising the neutralization site provided by the invention are made to induce measurable neutralizing antibodies. Especially sequences located at positions in the ORF 4 encoded protein of PRRSV corresponding to those found at about amino acid 40 to 79 as found in PRRSV isolate I-1102 comprise the neutralization site. Furthermore, selected peptide sequences are made even more immunogenic by mixing the peptides with adjuvants or other carriers known in the art. The thus obtained peptide compositions are used as a vaccine. However, also the selected peptide sequences comprising the neutralization site are incorporated in vaccine vector systems, being either distinct recombinant vectors derived of heterologous viruses or bacteria, but the selected peptide sequences are also selectively incorporated in PRRSV vector viruses or vaccines derived thereof.

In a further aspect of the invention, amino acid sequences located at positions corresponding from about 52 to 75 more specifically constitute a broadly reactive neutralization site. Other embodiments of the neutralization site provided by the invention can be found among the various PRRSV isolates known or to be found (see for instance the experimental part of this description). It is easy for any person working in the field of molecular biology to compare the sequences comprising the neutralization site provided by the invention with the amino acid sequence of the ORF 4 encoded protein of yet another PRRSV isolate.

The invention also provides peptide sequences of PRRSV which improve diagnostic tests, be it antigen or antibody detection tests. The invention provides various groups of antigenic sites which are used alone or in combination in diagnostic tests. In this way diagnostic tests are provided by the invention that serve the various needs that exists in the field with regard to diagnosis and differential diagnosis. Antigen-antibody interactions always entail cross-reactive epitope-paratope interactions of amino acid sequences that are from 5 to 15 amino acid sequences long. Thus amino acid sequences of 5 to 15 amino acids long and partly or completely overlapping with the core sequences of the antigenic sites of invention are provided by the invention for incorporation in diagnostic tests. These peptide sequences are used to select or design antigen or antigenic substance containing the sequences in the test to be used. Alternatively, and provided by the invention, are synthetic antibodies reactive with the antigenic sites provided by the invention. These sites or related sequences react with synthetic antibody obtained from systems such as phage display libraries or clonal selection of (heavy chain) antibodies that constitute antibody-like molecules which can easily be expressed in heterologous expression systems.

One group provided by the invention comprises the peptide sequence corresponding to said neutralization site, as already explained above. Diagnostic tests comprising this site and/or antibodies specifically directed against this site detect neutralizing antibodies in the pig.

Another group provided by the invention comprises a conserved antigenic site on protein N. Within the conserved antigenic site the invention provides a core sequence VNQLCQLLGA (SEQ ID NO. 1) or VNQLCQMLGK (SEQ ID NO. 2). Diagnostic tests comprising this site and/or antibodies specifically directed against this site detect those antibodies in pigs that specifically react with most PRRSV isolates. Also, diagnostic tests are provided that use antibodies directed against the conserved site to detect the PRRSV antigen, thereby allowing the test to detect PRRSV isolates, irrespective of their origin.

Another group provided by the invention comprises a non-conserved differentiating antigenic site on protein N. Diagnostic tests comprising this site and/or antibodies specifically directed against this site detect those antibodies in pigs that specifically react with distinct PRRSV isolates, whereby for example vaccinated pigs can be discriminated from pigs infected with wild type PRRSV. Also, diagnostic tests are provided that use antibodies directed against the non-conserved site to detect the PRRSV antigen, thereby allowing the test to discern different PRRSV isolates. Within one such a non-conserved site the invention provides a core sequence PRGGQAKKKK (SEQ ID NO. 3) or PRGGQAKRKK (SEQ ID NO. 4) or PRGGQAKKRK (SEQ ID NO. 5) or GPGKKNKKKN (SEQ ID NO. 6) or GPGKKNKKKT (SEQ ID NO. 7) or GPGKKNRKKN (SEQ ID NO. 8) or GPGKKFKKKN (SEQ ID NO. 9) or GPGKKIKKKN (SEQ ID NO. 10) or GPGQINKKIN (SEQ ID NO. 11). Within another non-conserved site the invention provides a core sequence MAGKNQSQKK (SEQ ID NO. 12) or MPNNNGKQTE (SEQ ID NO. 13) or MPNNNGKQPK (SEQ ID NO. 14) or MPNNNGKQQK (SEQ ID NO. 15) or MPNNNGKQQN (SEQ ID NO. 16) or MPNNNGRQQK (SEQ ID NO. 17). Also, artificial changes that maintain the antigenicity and thus functionality of the above core sequences in the GP4 or N protein can easily be introduced by anyone skilled in the art of peptide design and synthesis, as described above.

The invention also provides a group comprising conformational epitopes (which vary greatly among the various isolates) which can be found at positions corresponding to those found in isolate I-1102 from amino acid position 51 to about 68 (in isolate I-1102 core sequence PKPHFPLAAEDDIRHHL) (SEQ ID NO. 18) or from 79 to about 90 (in isolate I-1102 core sequence SIQTAFNQGAGT) (SEQ ID NO. 19) or from 111 to 124 (in isolate I-1102 core sequence HTVRLIRVTSTSAS) (SEQ ID NO. 20) on protein N. The conserved and non-conserved and differentiating and conformational sites in the N protein, which sites are provided by the invention, provide diagnostic tests that unequivocally diagnose PRRSV infections. Tests are made that avoid employing non-conserved sites thereby avoiding false-negative results. In addition, the various non-conserved sites are used in the development of differentiating tests that can e.g. discriminate vaccinated pigs from pigs infected with wild type isolates of PRRSV. Again, as said it is easy for any person working in the field of molecular biology to align the sequences comprising the conserved or non-conserved or conformational epitope sites with amino acid sequences of the ORF 7 encoded protein of yet another PRRSV isolate. The sites provided by the invention are used in new pairs of vaccine-discriminating diagnostic tests for use in eradication programs of PRRS.

BRIEF DESCRIPTION OF THE FIGURES

FIG. 3 (i.e., FIGS. 3A & 3B) depicts the alignment of amino acid sequences of $GP_4$ (A) and N (B) proteins of various PRRSV strains. Only the amino acids which differ from the I-1102 sequence are shown. The core peptide sequences recognized by MAbs and/or polyclonal sera in pepscan analysis are underlined.

FIG. 4 depicts the location of antigenic binding sites in the N protein sequence and compares the N protein sequence with those of North American strain VR2332 and LDV.

Figure 1:
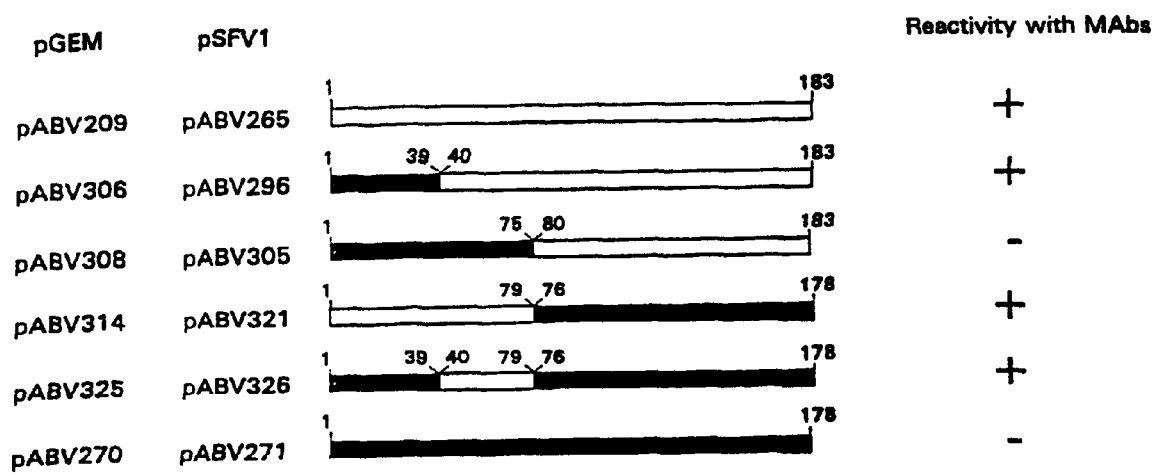
FIG. 1 is a schematic diagram of G proteins expressed in pS FV1 and their activity with GP4-specific MAbs. The names of the plasmids containing the different ORF4 genes are indicated. Open bars represent the amino acid sequences derived from the G protein coded by ORF4 of PRRSV, black bars represent amino acid sequences derived from G protein encoded by ORF4 of VR2332. The numbers of the amino acid are indicated above the bars. The genes were first inserted in PGEM-4Z and then transferred to PS FV1, as described in detail in the materials and methods section. The complete set of 14 GP4-specific MAbs reacted identically with the different constructs in IPMA and the reactivity is indicated as positive (+) and negative (−)
Figure 2A:
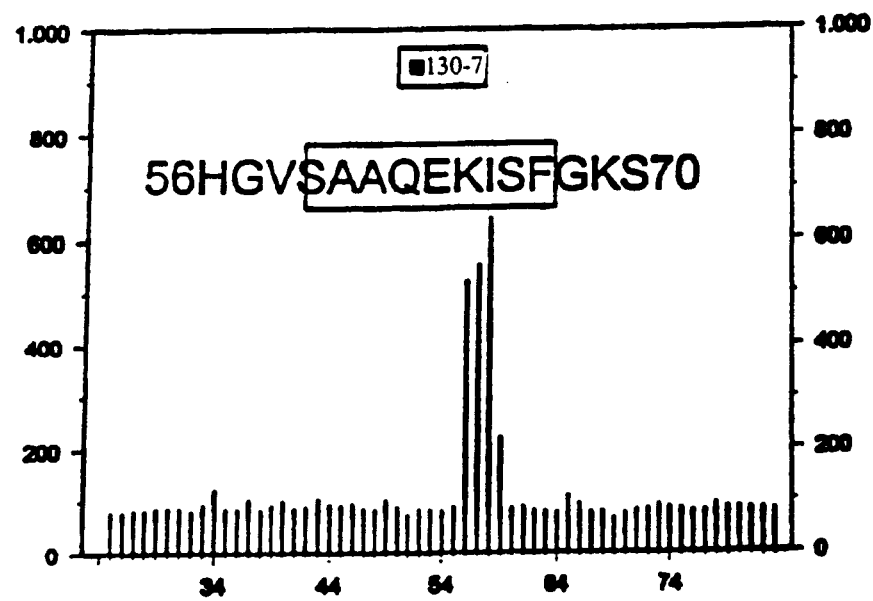
FIG. 2 (i.e., FIGS. 2A–2D) is a PEPSCAN analysis of $GP_4$-specific MAbs and polyclonal sera with overlapping 12-mer peptides covering residues 25 to 94 of $GP_4$. The scan of MAbs 130.7 and MAb 138.28 which recognize four consecutive peptides is shown (2A). Five other MAbs (122.29, 122.30, 122.66, 122.71 and 138.28) exhibited similar specificity. The scans of polyclonal sera from two pigs before immunization (va12-0 and va14-0), after immunization with a pseudorabies virus vector expressing ORF4 (va12-54 and va14-54) and after subsequent challenge with PRRSV (va12-sl an va14-sl) are shown (2A and 2B), and the scan of polyvalent porcine anti-LV serum 21 (va21) is shown (2D). The amino acid sequence of the reactive peptides is shown with the core of common residues boxed.
Figure 2A:
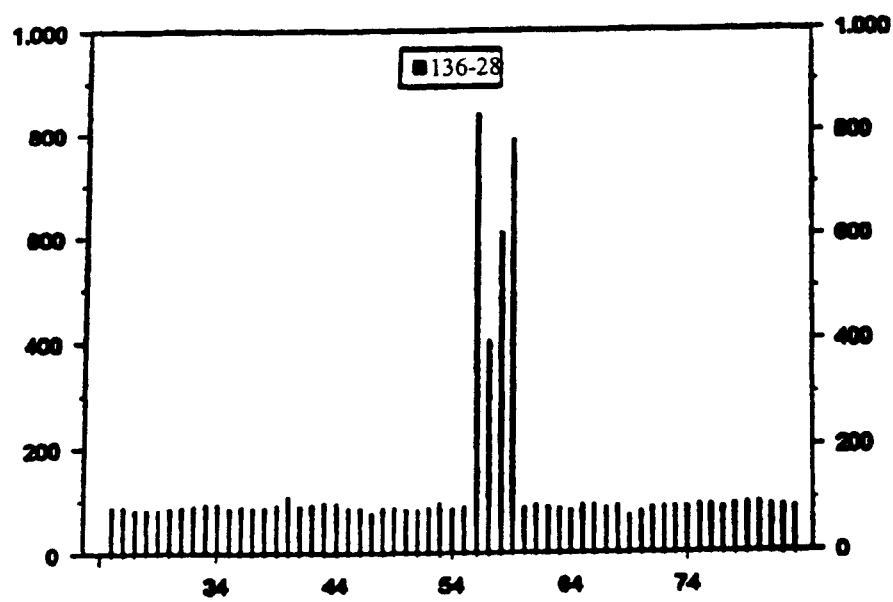
Figure 2B:
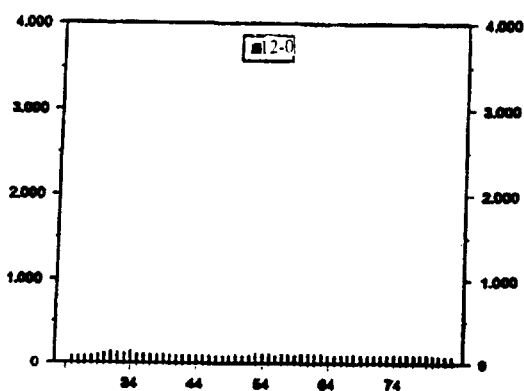
Figure 2B:
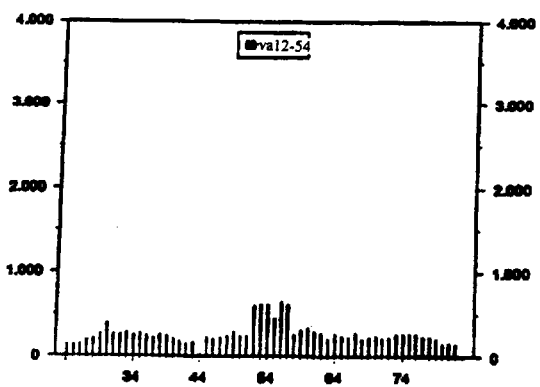
Figure 2B:
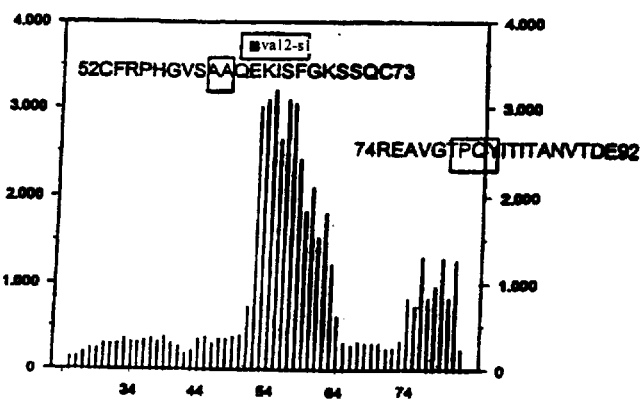
Figure 2C:
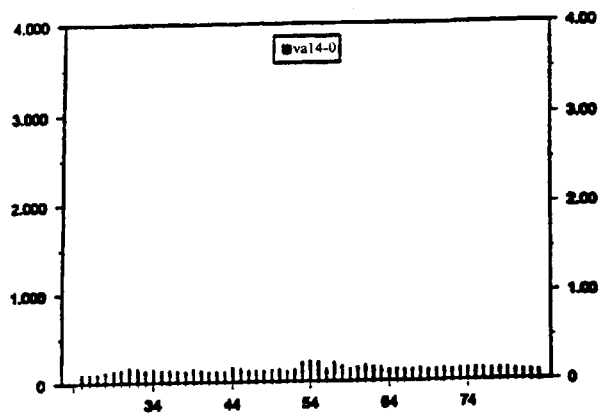
Figure 2C:
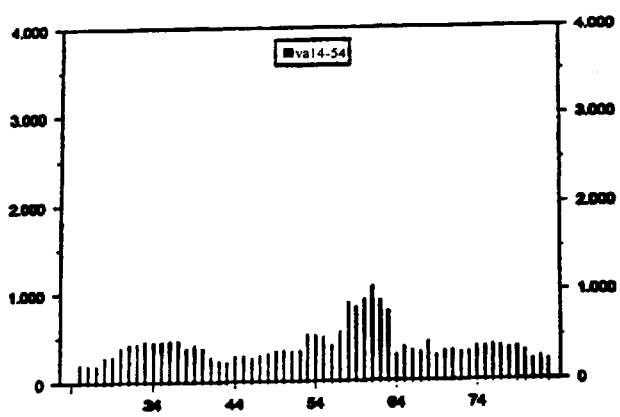
Figure 2C:
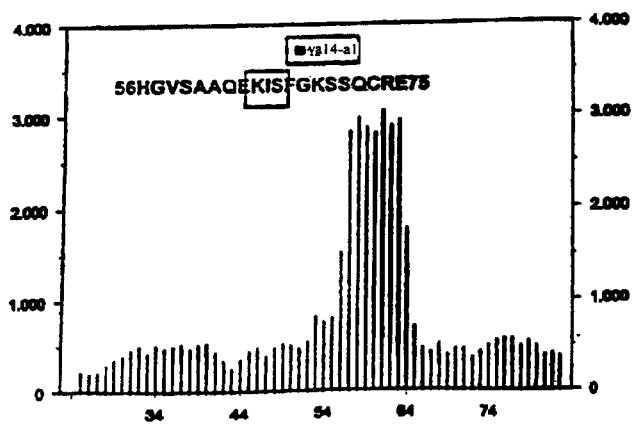
Figure 2D:
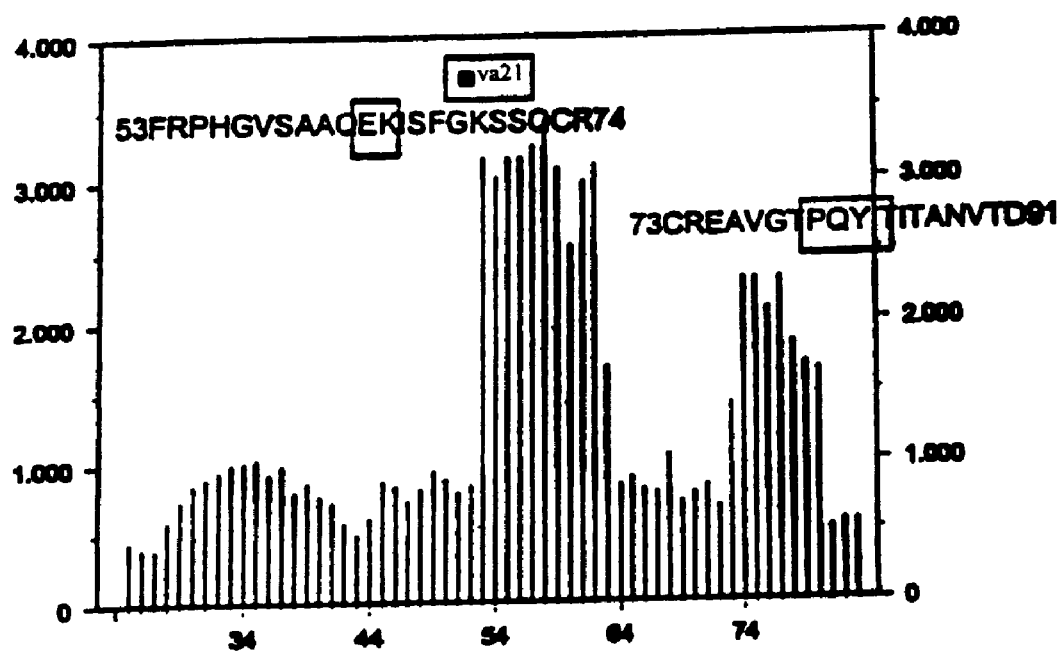

Antigenic sites A, B, C, and domain D are shown in shadow. Sites A, B, and C were identified in pepscan analysis, site D was identified by construction of chimeric N proteins. The amino acid sequences of LV that were substituted for the corresponding amino acid sequences of LDV in order to map domain D are underlined. The amino acids of the N protein of EAV that were inserted between amino acids 25–30 to mutate site B are shown below the LDV sequence. Identical amino acids are connected with vertical bars.

DETAILED DESCRIPTION OF THE INVENTION

The invention is further explained by the following illustrative Examples.

EXAMPLES

Experimental part
Materials and methods
Cells and viruses

The Ter Huurne strain (CNCM I-1102) of PRRSV was isolated in 1991 (Wensvoort et al., 1991). The U.S. ATCC-VR2332 strain was isolated by Benfield et al. (1992). Strain NL1 (Netherlands, 1991) was isolated in our lab, Strain NY2 (England, 1991) was kindly provided by T. Drew, strain DEN (Denmark, 1992) was kindly provided by A. Botner, strain LUX (Luxemburg, 1992) was kindly provided by Losch, SPA1 and SPA2 (Spain, 1992) were kindly provided by Shokouhi and Espuna, respectively, and strain FRA (France, 1992) was kindly provided by Y. Leforban.

PRRSV and VR2332 were grown on CL2621 cells as described previously (van Nieuwstadt et al, 1996). The seven different European isolates were grown in porcine alveolar macrophages. Macrophages were maintained as described before (Wensvoort et al, 1991). BHK-21 cells were maintained in Dulbecco's Minimal Essential Medium supplemented with 5% fetal bovine serum and antibiotics. For transfection experiments, BHK-21 cells were grown in Glasgow Minimal Essential Medium (GIBCO-BRL/Life Technologies Ltd).

Antisera.

Porcine anti-PRRSV serum 21 and rabbit anti-peptide sera 698 and 700 were used in previous experiments. Serum 700 is directed against amino acids 106 to 122 (CLFYASEMSEKGFKVIF) encoded by ORF4 of PRRSV and was obtained from a rabbit. The production and characterization of MAbs have been described (van Nieuwstadt et al, 1996). The hybridomas were derived from five consecutive fusion experiments and directed against ORF 4 protein (MAb 121.4, 122.1, 122.12, 122.20, 122.29, 122.30, 122.59, 122.66, 122.68, 122.70, 122.71, 126.1, 126.7, 130.7, 138.28)or ORF7 protein (MAb 122.17, 125.1, 126.9, 126.15, 130.2, 130.4, 131.7, 138.22, WBE1, WBE4, WBE5, WBE6, SDOW17) Mabs WBE were graciously provided by Dr. Drew, Weybridge, UK; Mab SDOW 17 was graciously provided by Dr. Benfield, South Dakota, U.S.

Plasmid Constructions

Two oligonucleotides located upstream (PRRSV 13) and downstream (PRRSV14) of ORF4 have been used earlier to amplify and clone ORF4 of isolate I-1102 in pGEM-4Z using the BarnHI and HindIII sites introduced in the primers (Meulenberg et al. 1995). The resulting plasmid was named pABV209. Two oligonucleotides located at a similar position with respect to the initiation codon (PRRSV4) and the termination codon (PRRSV5) of ORF4 of VR2332 were used to amplify ORF4 of VR2332 by means of RT-PCR as described in previous studies. The PCR fragment was digested with BamHI and partially with HindIII since ORF4 of VR2332 contains an internal HindIII site, and cloned in pGEM-4Z resulting in plasmid pABV270. Recombinant DNA techniques were performed essentially as described by Sambrook et al. (Molecular Cloning, A laboratory manual, Cold Spring Harbor Lab, Cold Spring Harbor, N.Y., 1989). The nucleotide sequence of VR2332 ORF4 in pABV270, determined on an automated DNA sequencer (Applied Biosystems), was identical to the published sequence (Murtaugh et al., Arch. Virol. 140; 1451–1460,1995). Subsequently, ORF4 of I-1102 and VR2332 were transferred to Semliki Forest virus expression vector pSFV1. pABV209 and pABV270 were digested with BamHI and HindIII (partially for pABV270), the ORF4 fragments were treated with Klenow polymerase (Pharmacia) to create blunt ends and these were ligated in the SmaI site of pSFV1, dephosphorylated with calf intestinal alkaline phosphatase (Pharmacia). Plasmids containing ORF4 of I-1102 (pABV265) and VR2332 (pABV271) in the correct orientation were further tested for expression of the $GP_4$ protein. In addition, four different chimeric ORF4 genes of I-1102 and VR2332 were made. The nucleotide sequence of ORF4 encoding amino acids 1 through 39 of the $GP_4$ protein of VR2332 was amplified from plasmid pABV270 with oligonucleotides PRRSV4 and PRRSV6. The obtained fragment was digested with BamHI and SacII. This fragment was ligated in pABV209 digested with BamHI and SacII to create an in frame fusion between amino acids 1 through 39 of the $GP_4$ protein of VR2332 and 40 through 183 of the $GP_4$ protein of I-1102 in pABV306. The nucleotide sequence of ORF4 encoding amino acids 1 through 75 of $GP_4$ of VR2332 was amplified with oligonucleotides PRRSV4 and PRRSV9 (see Table 2). This fragment was digested with KpnI and BamHI. The nucleotide sequence of ORF4 encoding amino acids 80 to 183 of the I-1102 $GP_4$ protein were amplified with PRRSV46 and PRRSV14 and the amplified fragment was digested with KpnI and BamHI. Both fragments were ligated together in pGEM-4Z digested with BamHI and HindIII, resulting in plasmid pABV308. In the same way a complementary construct was created in pABV314 consisting of the nucleotide sequence encoding amino acids 1 through 79 of the I-1102 GP4 protein amplified with PRRSV 13 and PRRSV57 ligated to a fragment encoding amino acids 76 through 178 of VR2332, which was amplified with PRRSV10 and PRRSV5, in pGEM-4Z. A fourth chimeric construct consisted of a fragment encoding amino acids 40 through 79 of the PRRSV $GP_4$ protein fused to fragments encoding amino acids 1 through 39 and amino acids 76 through 178 of the VR2332 $GP_4$ protein. This was achieved by ligating the BamHI/SacII ORF4 fragment of pABV270 and the SacII/HindIII ORF4 fragment of pABV314 in pGEM-4Z digested with BamHI and HindIII. This plasmid was designated pABV325. Plasmids pABV306, pABV308, pABV314, and pABV325 were checked for the correct sequence by oligonucleotide sequencing. The chimeric ORF4 genes were transferred from pABV306, pABV308, pABV314, and pABV325 to PSFVI, identical as described above for the ORF4 genes of VR2332 and PRRSV, resulting in pABV296, pABV305, pABV321, and pABV326, respectively (FIG. 3).

Two oligonucleotides located upstream (LV108;5' GGAGTGGTTAACCTCGTCAAGTATGGC-CGGTAAAAACCAGAGCC 3') (SEQ ID NO. 21) and downstream (LV112;5' CCATTCACCTGACTGTTTAAT-TAACTTGCACCCTGA 3') (SEQ ID NO. 22) of ORF7 were used to amplify and clone the ORF7 gene in pGEM-T, resulting in pABV431. The sequences and position of these and other oligonucleotides used to amplify fragments of ORF7 are listed in Table 1. In addition, four different chimeric constructs were made by PCR-directed mutagenesis. The sequences coding for amino acids 25–26, 28–30 (site B; FIG. 3) were substituted for the corresponding sequences of the EAV N protein. This was accomplished by PCR amplification of ORF7 with LV108 and LV134 (5' TGGGGAATGGCCAGCCAGTCAATGACCT-GTGCCGGATGTTTGGTGCAATGATAAA GTCC 3') (SEQ ID NO. 23). The mutated DNA fragment was introduced in pABV431 using the MscI and PacI site, which resulted in pABV455. The region of ORF7 encoding amino acids 51 to 67 was substituted for the corresponding region of LDV ORF7. pABV431 was digested with EcoNI and ClaI and ligated to a PCR fragment produced with primers LV98 (5' CCAGCAACCTAGGGGAGGACAGGC-CAAAAGAAAAAGCAGCCGAAGCTACATTT TCCCATGGCTGGTCCATCTGAC 3') (SEQ ID NO. 24) and LV99 (5' CGTCTGGATCGATTGCAAGCAGAGG-GAGCGTTCAGTCTGGGTGAGGACGTGCCGG AGGT-CAGATGGACCAGCC 3') (SEQ ID NO. 25), digested with the same enzymes. This plasmid was designated pABV463. The region of ORF7 encoding amino acids 80 to 90 was substituted for the corresponding region of the LDV ORF7 gene. The ORF7 gene of LV was mutated in a PCR with primers LV 101 (5' GCTTGCAGGCGCCCGT-GACGCTTTTCAATCAAGGCGGAGGACAG-GCGTCGCTTTCATCCA3') (SEQ ID NO. 26) and LV 112. The obtained fragment was digested with NarI and PacI and ligated to pABV43 1 digested with ClaI and PacI. This resulted in pABV453. Finally, the region encoding the C terminal part of the N protein (amino acids 111–128) was replaced for a sequence encoding the corresponding amino acids of the N protein of LDV. The ORF7 gene was amplified with primers LV 108 and LV 102 (5' ATGTC-CCGGGCTAAGCGGCGGAGGAATTAGCA-GAAGCGTTAATCAGGCGCTGTGT AGCAGCAACCG-GCAG 3') (SEQ ID NO. 27) and cloned in the pGEM-T vector, which resulted in pABV456. The wild type and mutated ORF7 genes were excised from pABV431, pABV453, pABV455, and pABV463 by digestion with PacI (blunt ended) and HpaI and from pABV456 by digestion with HpaI and SwaI. These genes were subsequently inserted in the dephosphorylated SmaI site of Semliki forest virus expression vector pSFV1. Plasmids pABV470, pABV460, pABV462, pABV518 and pABV471 containing the respective ORF7 genes in the correct orientation were further tested for expression of the N protein. In vitro transcription and transfection of Semliki forest virus ORF7 RNA was as described above for the SFV-ORF4 constructs.

To clone the ORF4 genes of seven different European isolates macrophages were infected with NL1, NY2, DEN, FRA, SPA1, SPA2, and LUX, and RNA was isolated as described by Meulenberg et al. (1993). The ORF4 genes were amplified by means of RT-PCR with oligonucleotides PRRSV 13 and PRRSV 14, and cloned with BamHI and HindIII in pGEM-4Z. For each strain, the nucleotide sequence of ORF4 of two clones derived from two independent PCRs was determined. The protein sequences derived from the nucleotide sequence were aligned using the multiple sequence alignment program CLUSTAL of PCGene (Intelligenetics Tm).

In Vitro Transcription and Transfection of SFV-ORF4 RNA.

pSFV1 plasmids containing different ORF4 constructs were linearized by digestion with SpeI and transcribed in vitro. The synthesized RNA was transfected to BHK-21 cells in 15 mm wells of twenty four-well plates using lipofectin. Cells were fixed with ice-cold 50% (v/v) methanol/aceton and the GP4 protein expressed by the different ORF4 constructs was stained with MAbs in the immunoperoxidase monolayer assay (IPMA). To analyze the ORF4 expression products by immunoprecipitation, $10^7$ BH K-21 cells were transfected with 10 mg in vitro transcribed SFV-ORF4 RNA by electroporation. The electroporated cells were plated in three 35 mm wells of six-well plates and 18 h after transfection cells were labeled.

Pepscan Method

A complete set of overlapping nonapeptides or dodecapeptides was synthesized from amino acids derived of the ORF4 or ORF7 sequence of PRRSV, as was determined previously (Meulenberg et al., 1993). The synthesis of solid-phase peptides on polyethylene rods and immunoscreening with an enzyme-linked immunosorbent assay (ELISA) type of analysis were carried out according to established PEPSCAN procedures (Geysen et al., PNAS, 81, 3998–4002, 1984).

RESULTS

We have previously described a panel of neutralizing MAbs that reacted with a 31 to 35 kDa protein of PRRSV, designated GP4, and a panel of Mabs reactive with the N protein, by Western immunoblot analysis. GP4 was shown to be a structural glycoprotein encoded by ORF4, N was shown to be the nucleocapsid protein encoded by ORF7. In immunoprecipitation experiments with $GP_4$ specific Mabs, the $GP_4$ protein derived from lysates of cells infected with PRRSV, migrated as a discrete band of 28 kDa together with a light smear of somewhat higher apparent molecular weight. The MAbs immunoprecipitated a diffuse (glycosylated) GP4 protein of about 31 kDa from the extracellular medium of PRRSV-infected but not from the extracellular medium of mock-infected cells.

Identification of the Neutralizing Domain in $GP_4$.

We have demonstrated earlier that MAbs specific for the $GP_4$ protein recognized I-1102 but not the U.S. isolate VR2332 (van Nieuwstadt et al., 1996). In order to identify the binding domain of the neutralizing MAbs in the $GP_4$ protein, we made fusion proteins of the $GP_4$ protein of I-1102 and VR2332. These proteins were expressed in the Semliki Forest virus expression system, developed by Liljeström et al. (Biotechnol, 9,1356–1362,1991). First, ORF4 of I-1102 was cloned in pSFV1 resulting in plasmid pABV265 (FIG. 1). RNA transcribed from pABV265 was transfected to BHK-21 cells and 24 h after transfection cells were positively stained with the panel of fifteen neutralizing MAbs. The MAbs did not react with BHK-21 cells transfected with pSFV1 -RNA. The recombinant $GP_4$ protein was immunoprecipitated with MAb 126.1 from L-[$^{35}$S]-methionine labeled BHK-21 cells transfected with pABV265 RNA. It had a similar size as the authentic GP, protein synthesized in CL2621 cells infected with I-1102 and also contained PNGaseF and EndoH sensitive N-glycans. The $GP_4$ protein of VR2332 was also cloned in pSFV1, but this protein was not recognized by the MAbs upon expression in BHK-21 cells (FIG. 1). To further localize the region in the $GP_4$ protein recognized by the MAbs, four chimeric genes of ORF4 of I-11022 and VR2332 were constructed in pSFVI (FIG. 1). RNA transcribed from plasmids pABV296, pABV305, pABV321, and pABV326 was transfected to BHK-21 cells and the reactivity of the expressed proteins with the $GP_4$-specific MAbs was tested in IPMA. The reaction pattern of these fifteen MAbs was identical, and indicated that these MAbs were directed to a region of 40 amino acids in the GP$_4$ protein; The expression product of pABV326, consisting of amino acids 40 through 79 derived from the GP4 protein of isolate CNCM I-1102 and surrounded by sequences derived from the VR2332 GP4 protein was still recognized by the panel of MAbs. To ensure that the different GP4 proteins, especially those which were not recognized by the MAbs, were properly expressed in BHK21 cells, they were immunoprecipitated from lysates of BHK-21 cells that were transfected with RNA transcribed in vitro from plasmids pABV265, pABV271, pABV296, pABV305, pABV321, and pABV326. Immunoprecipitation was carried out with porcine anti-PRRSV serum 21, MAb 126.1, and anti-peptide sera 698 and 700. Serum 700 is directed against amino acids 106–122 of the PRRSV GP4 protein of isolate CNCN I-1102, a sequence which is identical in the GP4 protein of isolate ATCC-VR2332, apart from amino acid 121. Therefore all GP4 proteins were immunoprecipitated with serum 700. They were indistinguishable in size, when analyzed by SDS-PAGE, except for the GP4 proteins expressed by pABV305 and pABV271, which migrated slightly faster. This is most likely due to the deletion of 4 amino acids in the VR2332 sequence relative to the I-1102 sequence, between amino acids 62–64 (FIG. 3). The complete set of GP4-specific MAbs recognized the GP4 proteins expressed from pABV265, pABV296, pABV321, pABV326, but not those expressed from pABV305 and pABV27 1, which confirmed the results obtained by IPMA (FIG. 3). Serum 698 had the same reaction profile as the MAbs. Serum 698 is directed against amino acids 62 to 77 of GP4 of PRRSV, which are located within the now identified neutralization domain of the GP4 protein. This region is highly heterogeneous in VR2332 ORF4, and therefore the expression products containing the VR2332 sequence in this region were not recognized by this serum. However, neutralizing polyclonal pig sera recognize the I-1102 GP4 protein and the chimeric GP4 proteins and the VR2332 GP4 protein, indicating that in porcine anti-PRRSV sera a variety of neutralizing antibodies that are directed against the neutralization site formed by amino acids 40 to 79 of the GP$_4$ protein are present.

Pepscan of the ORF4 and ORF7 Protein

Since the fifteen MAbs reactive with the ORF4 protein all reacted with the GP4 protein in western blot analysis, they were expected to recognize a linear epitope in a region spanning amino acids 40 through 79 of GP4 of isolate I-1102. To further map the binding region of the MAbs, a PEPSCAN analysis was performed using overlapping nonapeptides oe dodecapeptides in this region. Peptides were considered to represent antigenic sites if peaks in such a set reproducibly amounted to more than twice the background. MAbs 122–29, 122–30, 122–66, 122–71, 130–7, 138–28 reacted positively with one specific antigenic site consisting of amino acids 59 through 67 (SAAQEKISF) (SEQ ID NO. 28) (FIG. 2). MAb 122–12 reacted only weakly to this antigenic site, whereas the remaining 7 MAbs were negative in the PEPSCAN analysis. Polyclonal pig sera also identified this site in PEPSCAN. Neutralizing serum 21, taken at week 6 after infection of pig 21 with PRRSV reacted strongly and broadly with the site and its flanking regions. In addition, neutralizing polyclonal pig sera (va12 and va14), taken at 54 days after vaccination with PRV-ORF4 vector virus and at slaughter at 30 days after challenge at day 54 with PRRSV, reacted strongly and more broadly with the neutralization site identified in PEPSCAN.

In isolate I-1102, the core sequence of the neutralization site comprises the aa sequence SAAQEKISF (SEQ ID NO. 29) located from aa position 59–67. In other isolates the core sequence can be found at or around the corresponding aa position, which is an amino acid sequence corresponding to a neutralization site of protein GP$_4$, comprising for example sequences such as SAAQEEISF (SEQ ID NO. 30), or STAQENISF (SEQ ID NO. 31) or STAQENIPF (SEQ ID NO. 32) or SEESQSVT (SEQ ID NO. 33) or SASEAIR (SEQ ID NO. 34) or SASEAFR (SEQ ID NO. 35) or PAPEAFR (SEQ ID NO. 36) or PAPEAIR (SEQ ID NO. 37) or SAFETFR (SEQ ID NO. 38) or STSEAFR (SEQ ID NO. 39), but it is to be expected that other isolates of PRRSV have corresponding but slightly differing core sequences of the neutralization site located at or around the aa position corresponding to aa 59–67 of the ORF 4 amino acid sequence of the I-1102 isolate of PRRSV. Also, artificial changes that maintain the antigenicity and thus functionality of the above core sequences can easily be introduced by the average expert skilled in the art of peptide design and synthesis. Also, as is clearly demonstrated by the much broader reactivity in PEPSCAN of the neutralizing polyclonal sera, aa sequences comprising aa core sequences and aa sequences flanking the core sequences of the various PRRSV isolates in addition constitute the neutralization site on the ORF4 protein of PRRSV. Especially sequences located at positions corresponding to about aa 40 to 79 constitute the neutralization site (FIG. 1). Again, artificial changes that maintain the antigenicity and thus functionality of the above antigenic sites can easily be introduced by the average expert skilled in the art of peptide design and synthesis. Also, considering the broad reactivity of the polyclonal neutralizing sera va12 and va14 (FIG. 2), aa sequences located at positions corresponding from about aa 52 to 75 more specifically constitute a broadly reactive neutralization site.

The Mabs directed against the ORF7 protein reacted in four different groups in PEPSCAN, group A(4), B(2), C(3) and D(1). Group 1(D) (in which among others Mabs 122.17, 130.3, 130.4, 131.7, WBE1, WBE4, WBE6, SDOW17 and comprising conserved and non-conserved reactive sites) reacted with a conformational epitope not detectable in PEPSCAN. Group 2(B) (in which among others 125.1, 126.9, NS95 and NS99 and reactive with all isolates of PRRSV tested, thus identifying a conserved antigenic site) identifies a core sequence VNQLCQLLGA (SEQ ID NO. 1) (found in isolate I-1102 from aa position 22 to about 32) or VNQLCQMLGK (SEQ ID NO. 2). Group 3(C) (in which among others Mab 126.15 and mainly reactive with strains of PRRSV isolated in Europe, thus identifying a differentiating antigenic site) identifies a core sequence PRGGQAKKKK (SEQ ID NO. 3) (found in isolate I-1102 from aa position 41 to about 50) or PRGGQAKRKK (SEQ ID NO. 4) or PRGGQAKKRK (SEQ ID NO. 5) or GPGKKNKKKN (SEQ ID NO. 6) or GPGKKNKKKT (SEQ ID NO. 7) or GPGKKNRKKN (SEQ ID NO. 8) or GPGKKFKKKN (SEQ ID NO. 9) or GPGKKIKKKN (SEQ ID NO. 10) or GPGQINKKIN (SEQ ID NO. 11). Group 4(A) (in which among others Mab 138.22 and mainly reactive with strains of PRRSV isolated in Europe, thus identifying a differentiating antigenic site) identifies a core sequence MAGKNQSQKK (SEQ ID NO. 12) (found in isolate I-1102 from aa position 1 to about 10) or MPNNNGKQTE (SEQ ID NO. 13) or MPNNNGKQPK (SEQ ID NO. 14) or MPNNNGKQQK (SEQ ID NO. 15) or MPNNNGKQQN (SEQ ID NO. 16) or MPNNNGKQQK (SEQ ID NO. 17). Also, artificial changes that maintain the antigenicity and thus functionality of the above antigenic sites in the N protein can easily be introduced by the average expert skilled in the art of peptide design and synthesis.

Although group 1 does not constitute linear epitopes, comparison of PRRSV aa sequences with LDV sequences shows that conformational epitopes (which vary greatly among the various isolates) can be found at positions corresponding to those found in isolate I-1102 from aa position 51 to about 68 (in isolate I-1102 aa sequence PKPHFPLAAEDDIRHHL) (SEQ ID NO. 18) or from 79 to about 90 (in isolate I-1102 aa sequence SIQTAFNQGAGT) (SEQ ID NO. 19) or from 111 to 124 (in isolate I-1102 aa sequence HTVRLIRVTSTSAS) (SEQ ID NO. 20). Also, artificial changes that maintain the antigenicity and thus functionality of the above conformative epitope sites in the N protein can easily be introduced by the average expert skilled in the art of peptide design and synthesis, especially with information gathered by sequence comparison of PRRSV isolates, and by comparison with N protein sequences of other Arteriviridae. This was determined in expressing chimeric LDV/PRRSV ORF7 proteins in the SFV expression system (done as above for ORF4) and determining their reactivity with Mabs from group 1.

Chimeric N Proteins

Domain D was further mapped with constructs of ORF7 expressing chimeric N proteins. Since 6 out of 10 MAbs directed against domain D recognized both European and North American isolates of PRRSV, the regions which were most conserved between the N protein of LV and the North American prototype VR2332 (FIG. 4) were mutated. The nucleotide sequence coding for amino acids 51 to 67, 80 to 90, and 111 to 128 was substituted for a sequence that codes for the corresponding amino acids of LDV (FIG. 4). For completion, site B (amino acids 25–30) that is also conserved in European and North American isolates, was mutated. Since the amino acid sequence of the LV N protein was very similar to that of the LDV N protein in site B, this region of the LV N protein was substituted for a region encoding the corresponding amino acids of the EAV N protein (FIG. 4). When the mutated and wild type N proteins were expressed in BHK-21 cells using the Semliki forest virus expression system, and they were tested with the N-specific MAbs in IPMA, the D-specific MAbs reacted identical (Table 1). Their binding was disrupted by mutations between amino acids 51–67 and 80–90, but not by mutations between amino acids 111–128 or amino acids 25–30 (site B). As was expected, the N proteins with LDV sequences between amino acids 51–67 and 80–90 were still stained by MAbs directed against sites A, B, and C. However, the number of cells that were stained and the brightness of this staining was less than that observed for the wild type N protein and the N proteins mutated in amino acids 25–30 (site B) or in amino acids 111–128 (Table 1). This was most likely due to a lower expression of the N proteins containing mutations between amino acids 51–67 or 80–90, since a lower yield of these mutant N proteins compared to the other N proteins was also obtained when equal amounts of transcripts were translated in vitro (data not shown). As was expected, the N protein that contained EAV sequences in site B was not recognized by MAbs mapped to site B (by pepscan analysis), but was still recognized by MAbs that mapped to sites A, C, or domain D. These data indicate that the epitopes mapped to domain D are conformation-dependent and consist (partially) of amino acids 51–67 and 80–90.

Sequence Analysis of the $GP_4$ Protein of Different PRRSV Strains.

To analyze whether the major antigenic neutralization site, recognized by the $GP_4$-specific antibodies, was conserved among different PRRSV isolates, the reactivity and neutralizing activity of the MAbs was further tested on seven different European strains. The results indicated that these MAbs recognized and neutralized another Dutch strain NL1 and an English strain NY, but not Danish isolate DEN, two Spanish strains SPA1 and SPA2, a French isolate FRA, and LUX isolated in Luxembourg. Therefore we were interested in the amino acid sequence, in the region of the neutralization site of the $GP_4$ protein of these isolates. The ORF4 genes were cloned by means of RT-PCR using primers derived from the PRRSV sequence and the nucleotide sequence was determined. The amino acid sequence of the $GP_4$ protein of the different isolates derived from this nucleotide sequence were 86 to 97% identical with that of I-1102. The alignment of these amino acid sequences showed that the neutralization site (amino acids 40 through 79) is much more divergent than the remaining part of the protein. In this region, especially the amino acid sequences of strains DAN, SPA1, SPA2 and FRA are different. This is in line with the finding that these strains are not neutralized by the I-1102 specific MAbs and further confirms that this site is not highly conserved among European isolates. Another region of higher heterogeneity was observed in the N-terminal part of the $GP_4$ protein. Comparison of the amino acid sequence of the PRRSV $GP_4$ protein and that of VR2332 and other North American strains shows that the latter are also heterogenous in the neutralization site of the protein. Alignment of the amino acid sequences results in the introduction of a gap in the neutralization site of the North American isolates (FIG. 3), which is in agreement with the observation that none of these isolates are recognized by the MAbs. Overall, a higher diversity was observed among the sequences of the American isolates than among the sequences of the European isolates.

This is in line with the features characteristic for typical viral envelope, identified e.g. in the amino acid sequence of $GP_4$.

The potential of the neutralization site for vaccine development is of great importance in view of the heterogenicity of the neutralization site. Comparison of the amino acid sequence of the $GP_4$ proteins of different European strains indicated that the neutralization site was much more variable than other parts of the protein, suggesting that this site is susceptible to immunoselection. Comparison of the neutralization site sequences of European and North American strains displayed a gap of 4 amino acids in the North American sequences with respect to the European, further illustrating the large amino acid variability of the now identified neutralization site of PRRSV.

The neutralization site in the $GP_4$ protein described here, is the first site identified for Lelystad virus. For two other arteriviruses, EAV and LDV, the neutralizing MAbs that were isolated, were all directed against the $G_1$/VP3 protein encoded by ORF5 (Deregt et al, 1994; Glaser et al, 1995; Balasuriya et al, 1995; Harty and Plagemann, 1988). Using neutralization-escape mutants, the neutralization site of EAV was mapped to specific amino acids in the ectodomain of $G_1$.

Similar sequence comparisons were done for the ORF7 protein of PRRSV (FIG. 4) further illustrating the large amino acid variability of the now identified antigenically conserved site and non-conserved sites of PRRSV. In this work we have identified four distinct antigenic sites in the N protein of PRRSV. Three sites, designated A, B, and C contain linear epitopes and these were mapped between amino acids 2–12, 25–30, and 40–46, respectively. In contrast, the fourth site, designated domain D, contains conformation-dependent epitopes that are (partially) composed of amino acids 51–67 and 80–90. Sites A and C contain epitopes that are conserved in European but not in North American isolates of PRRSV, site B contains epitopes that are conserved in European and North American isolates of PRRSV, whereas site D contains both epitopes that are conserved and not conserved in European and North American isolates of PRRSV. The conserved sites in the N protein described here, are of great importance in the development of diagnostic tests aimed at unequivocal diagnosis of PRRSV infections, these tests should avoid employing non-conserved sites thereby avoiding false-negative results. In addition, knowledge about the various non-conserved sites is highly valuable in the development of differentiating tests that can e.g. discriminate vaccinated pigs from pigs infected with wild type isolates of PRRSV.

Table 2. Sequence of primers used in PCR to clone the ORF4 genes of LV and VR2332 and chimeric ORF-4 genes in plasmid vectors pGEM-4Z and pSFV1

| Name | Sequence[a] | Incorporated restriction site |
| --- | --- | --- |
| LV13 | 5' GGCAATT*GGATCC*ATTTGGA 3' (SEQ ID NO.40) | BamHI |
| LV14 | 5' AGAAGCA*AGCTT*GCGGAGTC 3' (SEQ ID NO.41) | HindIII |
| LV46 | 5' GCCGTC*GGTACC*CCTCAGTACAT 3' (SEQ ID NO.42) | KpnI |
| LV57 | 5' ATGTACTGAGG*GGTACC*GACGGC 3' (SEQ ID NO.43) | KpnI |
| PRRSV4 | 5' GGCAATT*GGATCC*ACCTAGAATGGC 3' (SEQ ID NO.44) | BamHI |
| PRRSV5 | 5' GCGAGCA*AGCTT*CCGCGGTCAAGCATTTCT 3' (SEQ ID NO.45) | HindIII |
| PRRSV6 | 5' CTTGCCG*CCGCGG*TGGTGTTG 3' (SEQ ID NO.46) | SacII |
| PRRSV9 | 5' A*CAGCTGGTACC*TATCGCCGTACGGCACTGA 3' (SEQ ID NO.47) | KpnI |
| PRRSV10 | 5' GCGATAGG*TACC*CCTGTGTATGTTACCAT 3' (SEQ ID NO.48) | KpnI |

[a]The underlined nucleotides in these primers are mutated with respect to the original sequence to create restriction sites or overhanging sequences or to avoid long stretches of one particular nucleotide. The restriction sites in the primers are shown in italics.

What is claimed is:

1. A synthetic peptide that elicits antibodies that react with at least two different PRRSV isolates, said synthetic peptide comprising an amino acid sequence of at least 10 to about 15 amino acid residues completely overlapping a conserved site of protein N of PRRSV wherein said conserved site comprises the amino acid residues located at amino acid position 22 to 32 of protein N of PRRSV isolate I-1102.

2. The synthetic peptide of claim 1, wherein one or more of said amino acid residues of said amino acid sequence have been replaced while retaining said synthetic peptide's ability to elicit said antibodies.

3. A synthetic peptide that elicits antibodies which antibodies react with at least two different PRRSV isolates, said synthetic peptide comprising an amino acid sequence of at least about 5 to about 15 amino acid residues partly or completely overlapping a conserved site of protein N of PRRSV wherein said amino acid sequence is selected from the group consisting of SEQ ID NO. 1 and SEQ ID NO. 2.

* * * * *

SEQUENCE LISTING

```
<160> NUMBER OF SEQ ID NOS: 48

<210> SEQ ID NO 1
<211> LENGTH: 10
<212> TYPE: PRT
<213> ORGANISM: Porcine reproductive and respiratory syndrome virus

<400> SEQUENCE: 1

Val Asn Gln Leu Cys Gln Leu Leu Gly Ala
1               5                   10

<210> SEQ ID NO 2
<211> LENGTH: 10
<212> TYPE: PRT
<213> ORGANISM: Porcine reproductive and respiratory syndrome virus

<400> SEQUENCE: 2

Val Asn Gln Leu Cys Gln Met Leu Gly Lys
1               5                   10

<210> SEQ ID NO 3
<211> LENGTH: 10
<212> TYPE: PRT
<213> ORGANISM: Porcine reproductive and respiratory syndrome virus

<400> SEQUENCE: 3

Pro Arg Gly Gly Gln Ala Lys Lys Lys Lys
1               5                   10

<210> SEQ ID NO 4
<211> LENGTH: 10
<212> TYPE: PRT
<213> ORGANISM: Porcine reproductive and respiratory syndrome virus

<400> SEQUENCE: 4

Pro Arg Gly Gly Gln Ala Lys Arg Lys Lys
```

-continued

```
1               5                   10

<210> SEQ ID NO 5
<211> LENGTH: 10
<212> TYPE: PRT
<213> ORGANISM: Porcine reproductive and respiratory syndrome virus

<400> SEQUENCE: 5

Pro Arg Gly Gly Gln Ala Lys Lys Arg Lys
1               5                   10

<210> SEQ ID NO 6
<211> LENGTH: 10
<212> TYPE: PRT
<213> ORGANISM: Porcine reproductive and respiratory syndrome virus

<400> SEQUENCE: 6

Gly Pro Gly Lys Lys Asn Lys Lys Lys Asn
1               5                   10

<210> SEQ ID NO 7
<211> LENGTH: 10
<212> TYPE: PRT
<213> ORGANISM: Porcine reproductive and respiratory syndrome virus

<400> SEQUENCE: 7

Gly Pro Gly Lys Lys Asn Lys Lys Lys Thr
1               5                   10

<210> SEQ ID NO 8
<211> LENGTH: 10
<212> TYPE: PRT
<213> ORGANISM: Porcine reproductive and respiratory syndrome virus

<400> SEQUENCE: 8

Gly Pro Gly Lys Lys Asn Arg Lys Lys Asn
1               5                   10

<210> SEQ ID NO 9
<211> LENGTH: 10
<212> TYPE: PRT
<213> ORGANISM: Porcine reproductive and respiratory syndrome virus

<400> SEQUENCE: 9

Gly Pro Gly Lys Lys Phe Lys Lys Lys Asn
1               5                   10

<210> SEQ ID NO 10
<211> LENGTH: 10
<212> TYPE: PRT
<213> ORGANISM: Porcine reproductive and respiratory syndrome virus

<400> SEQUENCE: 10

Gly Pro Gly Lys Lys Ile Lys Lys Lys Asn
1               5                   10

<210> SEQ ID NO 11
<211> LENGTH: 10
<212> TYPE: PRT
<213> ORGANISM: Porcine reproductive and respiratory syndrome virus

<400> SEQUENCE: 11

Gly Pro Gly Gln Ile Asn Lys Lys Ile Asn
1               5                   10
```

```
<210> SEQ ID NO 12
<211> LENGTH: 10
<212> TYPE: PRT
<213> ORGANISM: Porcine reproductive and respiratory syndrome virus

<400> SEQUENCE: 12

Met Ala Gly Lys Asn Gln Ser Gln Lys Lys
1               5                   10

<210> SEQ ID NO 13
<211> LENGTH: 10
<212> TYPE: PRT
<213> ORGANISM: Porcine reproductive and respiratory syndrome virus

<400> SEQUENCE: 13

Met Pro Asn Asn Asn Gly Lys Gln Thr Glu
1               5                   10

<210> SEQ ID NO 14
<211> LENGTH: 10
<212> TYPE: PRT
<213> ORGANISM: Porcine reproductive and respiratory syndrome virus

<400> SEQUENCE: 14

Met Pro Asn Asn Asn Gly Lys Gln Pro Lys
1               5                   10

<210> SEQ ID NO 15
<211> LENGTH: 10
<212> TYPE: PRT
<213> ORGANISM: Porcine reproductive and respiratory syndrome virus

<400> SEQUENCE: 15

Met Pro Asn Asn Asn Gly Lys Gln Gln Lys
1               5                   10

<210> SEQ ID NO 16
<211> LENGTH: 10
<212> TYPE: PRT
<213> ORGANISM: Porcine reproductive and respiratory syndrome virus

<400> SEQUENCE: 16

Met Pro Asn Asn Asn Gly Lys Gln Gln Asn
1               5                   10

<210> SEQ ID NO 17
<211> LENGTH: 10
<212> TYPE: PRT
<213> ORGANISM: Porcine reproductive and respiratory syndrome virus

<400> SEQUENCE: 17

Met Pro Asn Asn Asn Gly Arg Gln Gln Lys
1               5                   10

<210> SEQ ID NO 18
<211> LENGTH: 16
<212> TYPE: PRT
<213> ORGANISM: Porcine reproductive and respiratory syndrome virus

<400> SEQUENCE: 18

Pro Lys Pro His Phe Pro Leu Ala Ala Glu Asp Asp Ile Arg His His
1               5                   10                  15

<210> SEQ ID NO 19
```

```
<211> LENGTH: 12
<212> TYPE: PRT
<213> ORGANISM: Porcine reproductive and respiratory syndrome virus

<400> SEQUENCE: 19

Ser Ile Gln Thr Ala Phe Asn Gln Gly Ala Gly Thr
1               5                   10

<210> SEQ ID NO 20
<211> LENGTH: 14
<212> TYPE: PRT
<213> ORGANISM: Porcine reproductive and respiratory syndrome virus

<400> SEQUENCE: 20

His Thr Val Arg Leu Ile Arg Val Thr Ser Thr Ser Ala Ser
1               5                   10

<210> SEQ ID NO 21
<211> LENGTH: 44
<212> TYPE: DNA
<213> ORGANISM: Porcine reproductive and respiratory syndrome virus

<400> SEQUENCE: 21
ggagtggtta acctcgtcaa gtatggccgg taaaaaccag agcc                    44

<210> SEQ ID NO 22
<211> LENGTH: 36
<212> TYPE: DNA
<213> ORGANISM: Porcine reproductive and respiratory syndrome virus

<400> SEQUENCE: 22
ccattcacct gactgtttaa ttaacttgca ccctga                             36

<210> SEQ ID NO 23
<211> LENGTH: 59
<212> TYPE: DNA
<213> ORGANISM: Porcine reproductive and respiratory syndrome virus

<400> SEQUENCE: 23
tggggaatgg ccagccagtc aatgacctgt gccggatgtt tggtgcaatg ataaagtcc    59

<210> SEQ ID NO 24
<211> LENGTH: 76
<212> TYPE: DNA
<213> ORGANISM: Porcine reproductive and respiratory syndrome virus

<400> SEQUENCE: 24
ccagcaacct aggggaggac aggccaaaaa gaaaaagcag ccgaagctac attttcccat   60
ggctggtcca tctgac                                                   76

<210> SEQ ID NO 25
<211> LENGTH: 73
<212> TYPE: DNA
<213> ORGANISM: Porcine reproductive and respiratory syndrome virus

<400> SEQUENCE: 25
cgtctggatc gattgcaagc agagggagcg ttcagtctgg gtgaggacgt gccggaggtc   60
agatggacca gcc                                                      73

<210> SEQ ID NO 26
<211> LENGTH: 60
<212> TYPE: DNA
<213> ORGANISM: Porcine reproductive and respiratory syndrome virus
```

```
<400> SEQUENCE: 26
gcttgcaggc gcccgtgacg cttttcaatc aaggcggagg acaggcgtcg ctttcatcca        60

<210> SEQ ID NO 27
<211> LENGTH: 70
<212> TYPE: DNA
<213> ORGANISM: Porcine reproductive and respiratory syndrome virus

<400> SEQUENCE: 27
atgtcccggg ctaagcggcg gaggaattag cagaagcgtt aatcaggcgc tgtgtagcag        60
caaccggcag                                                               70

<210> SEQ ID NO 28
<211> LENGTH: 9
<212> TYPE: PRT
<213> ORGANISM: Porcine reproductive and respiratory syndrome virus

<400> SEQUENCE: 28

Ser Ala Ala Gln Glu Lys Ile Ser Phe
1               5

<210> SEQ ID NO 29
<211> LENGTH: 9
<212> TYPE: PRT
<213> ORGANISM: Porcine reproductive and respiratory syndrome virus

<400> SEQUENCE: 29

Ser Ala Ala Gln Glu Lys Ile Ser Phe
1               5

<210> SEQ ID NO 30
<211> LENGTH: 9
<212> TYPE: PRT
<213> ORGANISM: Porcine reproductive and respiratory syndrome virus

<400> SEQUENCE: 30

Ser Ala Ala Gln Glu Glu Ile Ser Phe
1               5

<210> SEQ ID NO 31
<211> LENGTH: 9
<212> TYPE: PRT
<213> ORGANISM: Porcine reproductive and respiratory syndrome virus

<400> SEQUENCE: 31

Ser Thr Ala Gln Glu Asn Ile Ser Phe
1               5

<210> SEQ ID NO 32
<211> LENGTH: 9
<212> TYPE: PRT
<213> ORGANISM: Porcine reproductive and respiratory syndrome virus

<400> SEQUENCE: 32

Ser Thr Ala Gln Glu Asn Ile Pro Phe
1               5

<210> SEQ ID NO 33
<211> LENGTH: 9
<212> TYPE: PRT
<213> ORGANISM: Porcine reproductive and respiratory syndrome virus

<400> SEQUENCE: 33
```

Ser Glu Glu Gln Ser Gln Ser Val Thr
1               5

<210> SEQ ID NO 34
<211> LENGTH: 7
<212> TYPE: PRT
<213> ORGANISM: Porcine reproductive and respiratory syndrome virus

<400> SEQUENCE: 34

Ser Ala Ser Glu Ala Ile Arg
1               5

<210> SEQ ID NO 35
<211> LENGTH: 7
<212> TYPE: PRT
<213> ORGANISM: Porcine reproductive and respiratory syndrome virus

<400> SEQUENCE: 35

Ser Ala Ser Glu Ala Phe Arg
1               5

<210> SEQ ID NO 36
<211> LENGTH: 7
<212> TYPE: PRT
<213> ORGANISM: Porcine reproductive and respiratory syndrome virus

<400> SEQUENCE: 36

Pro Ala Pro Glu Ala Phe Arg
1               5

<210> SEQ ID NO 37
<211> LENGTH: 7
<212> TYPE: PRT
<213> ORGANISM: Porcine reproductive and respiratory syndrome virus

<400> SEQUENCE: 37

Pro Ala Pro Glu Ala Ile Arg
1               5

<210> SEQ ID NO 38
<211> LENGTH: 7
<212> TYPE: PRT
<213> ORGANISM: Porcine reproductive and respiratory syndrome virus

<400> SEQUENCE: 38

Ser Ala Phe Glu Thr Phe Arg
1               5

<210> SEQ ID NO 39
<211> LENGTH: 7
<212> TYPE: PRT
<213> ORGANISM: Porcine reproductive and respiratory syndrome virus

<400> SEQUENCE: 39

Ser Thr Ser Glu Ala Phe Arg
1               5

<210> SEQ ID NO 40
<211> LENGTH: 20
<212> TYPE: DNA
<213> ORGANISM: Unknown
<220> FEATURE:
<223> OTHER INFORMATION: Primer

<400> SEQUENCE: 40

```
ggcaattgga tccatttgga                                           20
```

<210> SEQ ID NO 41
<211> LENGTH: 20
<212> TYPE: DNA
<213> ORGANISM: Unknown
<220> FEATURE:
<223> OTHER INFORMATION: Primer

<400> SEQUENCE: 41

```
agaagcaagc ttgcggagtc                                           20
```

<210> SEQ ID NO 42
<211> LENGTH: 23
<212> TYPE: DNA
<213> ORGANISM: Unknown
<220> FEATURE:
<223> OTHER INFORMATION: Primer

<400> SEQUENCE: 42

```
gccgtcggta ccctcagta cat                                        23
```

<210> SEQ ID NO 43
<211> LENGTH: 23
<212> TYPE: DNA
<213> ORGANISM: Unknown
<220> FEATURE:
<223> OTHER INFORMATION: Primer

<400> SEQUENCE: 43

```
atgtactgag gggtaccgac ggc                                       23
```

<210> SEQ ID NO 44
<211> LENGTH: 25
<212> TYPE: DNA
<213> ORGANISM: Unknown
<220> FEATURE:
<223> OTHER INFORMATION: Primer

<400> SEQUENCE: 44

```
ggcaattgga tccacctaga atggc                                     25
```

<210> SEQ ID NO 45
<211> LENGTH: 30
<212> TYPE: DNA
<213> ORGANISM: Unknown
<220> FEATURE:
<223> OTHER INFORMATION: Primer

<400> SEQUENCE: 45

```
gcgagcaagc ttccgcggtc aagcatttct                                30
```

<210> SEQ ID NO 46
<211> LENGTH: 21
<212> TYPE: DNA
<213> ORGANISM: Unknown
<220> FEATURE:
<223> OTHER INFORMATION: Primer

<400> SEQUENCE: 46

```
cttgccgccg cggtggtgtt g                                         21
```

<210> SEQ ID NO 47
<211> LENGTH: 31
<212> TYPE: DNA

```
<213> ORGANISM: Unknown
<220> FEATURE:
<223> OTHER INFORMATION: Primer

<400> SEQUENCE: 47
acagctggta cctatcgccg tacggcactg a                                31

<210> SEQ ID NO 48
<211> LENGTH: 29
<212> TYPE: DNA
<213> ORGANISM: Unknown
<220> FEATURE:
<223> OTHER INFORMATION: Primer

<400> SEQUENCE: 48
gcgataggta cccctgtgta tgttaccat                                   29
```